United States Patent
Safai et al.

(10) Patent No.: US 10,078,049 B2
(45) Date of Patent: Sep. 18, 2018

(54) APPARATUS, SYSTEM, AND METHOD FOR NON-DESTRUCTIVE TESTING OF AN OBJECT USING A LASER BEAM DIRECTED OUT OF A PLURALITY OF APERTURES

(71) Applicant: The Boeing Company, Chicago, IL (US)

(72) Inventors: Morteza Safai, Newcastle, WA (US); Kimberly D. Meredith, Newcastle, WA (US)

(73) Assignee: The Boeing Company, Chicago, IL (US)

(*) Notice: Subject to any disclaimer, the term of this patent is extended or adjusted under 35 U.S.C. 154(b) by 28 days.

(21) Appl. No.: 15/158,057

(22) Filed: May 18, 2016

(65) Prior Publication Data
US 2017/0336324 A1    Nov. 23, 2017

(51) Int. Cl.
*G01B 9/02* (2006.01)
*G01N 21/45* (2006.01)
*G01N 21/88* (2006.01)

(52) U.S. Cl.
CPC ............ *G01N 21/45* (2013.01); *G01N 21/88* (2013.01)

(58) Field of Classification Search
CPC ................................ G01N 21/45; G01N 21/88
See application file for complete search history.

(56) References Cited

U.S. PATENT DOCUMENTS

| | | | | |
|---|---|---|---|---|
| 4,360,271 A | * | 11/1982 | Downs | G01B 9/02079 356/493 |
| 4,493,605 A | * | 1/1985 | Cullen | E02F 3/404 294/68.23 |
| 4,693,605 A | * | 9/1987 | Sommargren | G01J 9/0215 356/487 |
| 4,765,715 A | * | 8/1988 | Matsudaira | G02B 27/106 359/583 |
| 5,355,218 A | * | 10/1994 | Matsuda | G01M 11/0271 356/520 |
| 5,870,191 A | * | 2/1999 | Shirley | G01B 11/24 356/477 |
| 6,606,160 B1 | * | 8/2003 | Hung | G01B 11/162 356/35.5 |
| 6,637,266 B1 | | 10/2003 | Froom | |
| 6,801,299 B2 | * | 10/2004 | Kremer | G02B 27/09 355/67 |
| 7,538,891 B1 | | 5/2009 | Mello et al. | |
| 9,234,740 B1 | | 1/2016 | Safai et al. | |
| 9,285,544 B2 | * | 3/2016 | Panotopoulos | G02B 6/4231 |

* cited by examiner

*Primary Examiner* — Hwa Lee
(74) *Attorney, Agent, or Firm* — Kunzler, PC

(57) ABSTRACT

Described herein is an apparatus for non-destructive testing that includes a cavity. The apparatus also includes an input element coupled with the cavity and configured to receive a laser beam and to direct the laser beam into the cavity. The apparatus additionally includes multiple output elements formed in the cavity and spaced apart along the cavity. Each output element of the multiple output elements is configured to direct a portion of the laser beam out of the cavity such that each portion of the laser beam directed out of a respective one of the multiple output elements has a substantially similar intensity.

20 Claims, 7 Drawing Sheets

APPARATUS, SYSTEM, AND METHOD FOR NON-DESTRUCTIVE TESTING OF AN OBJECT USING A LASER BEAM DIRECTED OUT OF A PLURALITY OF APERTURES

FIELD

This disclosure relates generally to testing structures, and more particularly to non-destructive testing of materials using shearography.

BACKGROUND

Non-destructive testing may be used to test materials. By using non-destructive testing, properties of a material may be analyzed without causing damage to the material. Certain non-destructive testing is performed using shearography. Shearography uses coherent light or coherent soundwaves to provide information about the quality of a material. In some instances, shearography uses a laser light to illuminate a surface area of an object and create a first pattern. The first pattern may be subtracted from a second pattern created when the laser light illuminates the object while the object is under a load. The result may be analyzed to determine whether there is a defect in the object.

Certain laser splitting devices may split a laser beam to produce illumination of an object that is not uniform. Accordingly, objects illuminated with such laser splitting devices may be difficult to analyze using shearography.

SUMMARY

The subject matter of the present application provides examples of an apparatus with output elements that output portions of an input laser beam each having substantially similar intensities, and associated methods for manufacturing, that overcome the above-discussed shortcomings of prior art techniques. The subject matter of the present application has been developed in response to the present state of the art, and in particular, in response to shortcomings of conventional laser devices used to perform shearography.

According to one example, an apparatus includes a cavity. The apparatus also includes an input element coupled with the cavity and configured to receive a laser beam and to direct the laser beam into the cavity. The apparatus additionally includes multiple output elements formed in the cavity and spaced apart along the cavity. Each output element of the multiple output elements is configured to direct a portion of the laser beam out of the cavity such that each portion of the laser beam directed out of a respective one of the multiple output elements has a substantially similar intensity.

In some implementations of the apparatus, each of the multiple output elements includes a material. The material of at least one of the output elements of the multiple output elements is different from that of at least another of the output elements of the multiple output elements.

According to certain implementations of the apparatus, a first output element of the multiple output elements includes a partially reflective material through which a first portion of the laser beam is directed out of the cavity and a second portion of the laser beam is reflected, a last output element of the multiple output elements includes a non-reflective material through which a remaining portion of the laser beam is directed out of the cavity, and the first portion of the laser beam and the remaining portion of the laser beam have substantially similar intensities.

In certain implementations of the apparatus, a first output element of the multiple output elements includes a first partially reflective material that directs a first portion of the laser beam out of the cavity, a second output element of the multiple output elements includes a second partially reflective material that directs a second portion of the laser beam out of the cavity, the first and second partially reflective materials include different reflective properties, and the first portion of the laser beam and the second portion of the laser beam have substantially similar intensities.

According to yet some implementations of the apparatus, the first portion of the laser beam is directed out of the cavity before the second portion of the laser beam is directed out of the cavity, the first portion of the laser beam includes a first percentage of the laser beam, a remaining laser beam remains in the cavity after the first portion of the laser beam is directed out of the cavity, the second portion of the laser beam includes a second percentage of the remaining laser beam, and the second percentage is greater than the first percentage.

According to some implementations of the apparatus, the cavity is enclosed. In certain implementations of the apparatus, each output element of the multiple output elements is spaced apart from an adjacent output element of the multiple output elements by a substantially equal distance.

In various implementations of the apparatus, the cavity includes a first side and a second side opposite the first side, the input element is disposed on the first side of the cavity, and the multiple output elements are disposed on the second side of the cavity.

In certain implementations of the apparatus, the first side of the cavity includes a reflective coating. In some implementations of the apparatus, the second side of the cavity includes a partially reflective material having an opacity that varies from a first opacity to a second opacity, the first opacity being higher than the second opacity.

In another example, a system includes a laser selectively operable to generate a laser beam. The system includes an apparatus including a cavity, an input element coupled with the cavity and configured to receive the laser beam and to direct the laser beam into the cavity, and multiple output elements formed in the cavity and spaced apart along the cavity. Each output element of the multiple output elements is configured to direct a portion of the laser beam out of the cavity such that each portion of the laser beam directed out of a respective one of the multiple output elements has a substantially similar intensity. The system also includes at least one laser beam diverter configured to diffuse the portion of the laser beam that exits each output element of the multiple output elements.

According to some implementations of the system, the at least one laser beam diverter includes multiple laser beam diverters each configured to diffuse the portion of the laser beam that exits a respective one of multiple output elements.

In certain implementations of the system, the system includes at least one polarizer positioned between the multiple output elements and the laser beam diverter. The at least one polarizer is configured to polarize the portion of the laser beam that exits each output element of the multiple output elements. In some implementations of the system, the at least one polarizer is configured to polarize the portion of the laser beams that exit the multiple output elements to be polarized in a substantially similar direction. In various implementations of the system, the polarizer is configured to polarize the portion of the laser beam that exits each output element to be polarized in multiple directions.

According to some implementations of the system, the system includes a camera positioned to capture an image illuminated by the portions of the laser beams exiting the multiple output elements.

In some implementations of the system, the portions of the laser beams exiting the multiple output elements have a substantially similar phase.

According to yet another example, a method of non-destructive testing of an object includes illuminating an object using an apparatus. The apparatus includes a cavity, an input element coupled with the cavity and configured to receive a laser beam and to direct the laser beam into the cavity, and multiple output elements formed in the cavity and spaced apart along the cavity. Each output element of the multiple output elements is configured to direct a portion of the laser beam out of the cavity such that each portion of the laser beam directed out of a respective one of the multiple output elements has a substantially similar intensity. The method also includes capturing an image of the object illuminated by each portion of the laser beam directed out of the respective ones of the multiple output elements. The method includes analyzing the image to determine whether the object has a defect.

In some implementations of the method, analyzing the image to determine whether the object has a defect includes measuring out-of-plane displacement.

According to certain implementations of the method, measuring the out-of-plane displacement includes using image subtraction to subtract a change in a surface of the object detected via optical fringes.

The described features, structures, advantages, and/or characteristics of the subject matter of the present disclosure may be combined in any suitable manner in one or more examples and/or implementations. In the following description, numerous specific details are provided to impart a thorough understanding of examples of the subject matter of the present disclosure. One skilled in the relevant art will recognize that the subject matter of the present disclosure may be practiced without one or more of the specific features, details, components, materials, and/or methods of a particular example or implementation. In other instances, additional features and advantages may be recognized in certain examples and/or implementations that may not be present in all examples or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific examples that are illustrated in the appended drawings. Understanding that these drawings depict only examples of the subject matter, they are not therefore to be considered to be limiting of its scope. The subject matter will be described and explained with additional specificity and detail through the use of the drawings, in which.

DETAILED DESCRIPTION

Reference throughout this specification to "one example," "an example," or similar language means that a particular feature, structure, or characteristic described in connection with the example is included in at least one example of the present disclosure. Appearances of the phrases "in one example," "in an example," and similar language throughout this specification may, but do not necessarily, all refer to the same example. Similarly, the use of the term "implementation" means an implementation having a particular feature, structure, or characteristic described in connection with one or more examples of the present disclosure, however, absent an express correlation to indicate otherwise, an implementation may be associated with one or more examples.

Figure 1:
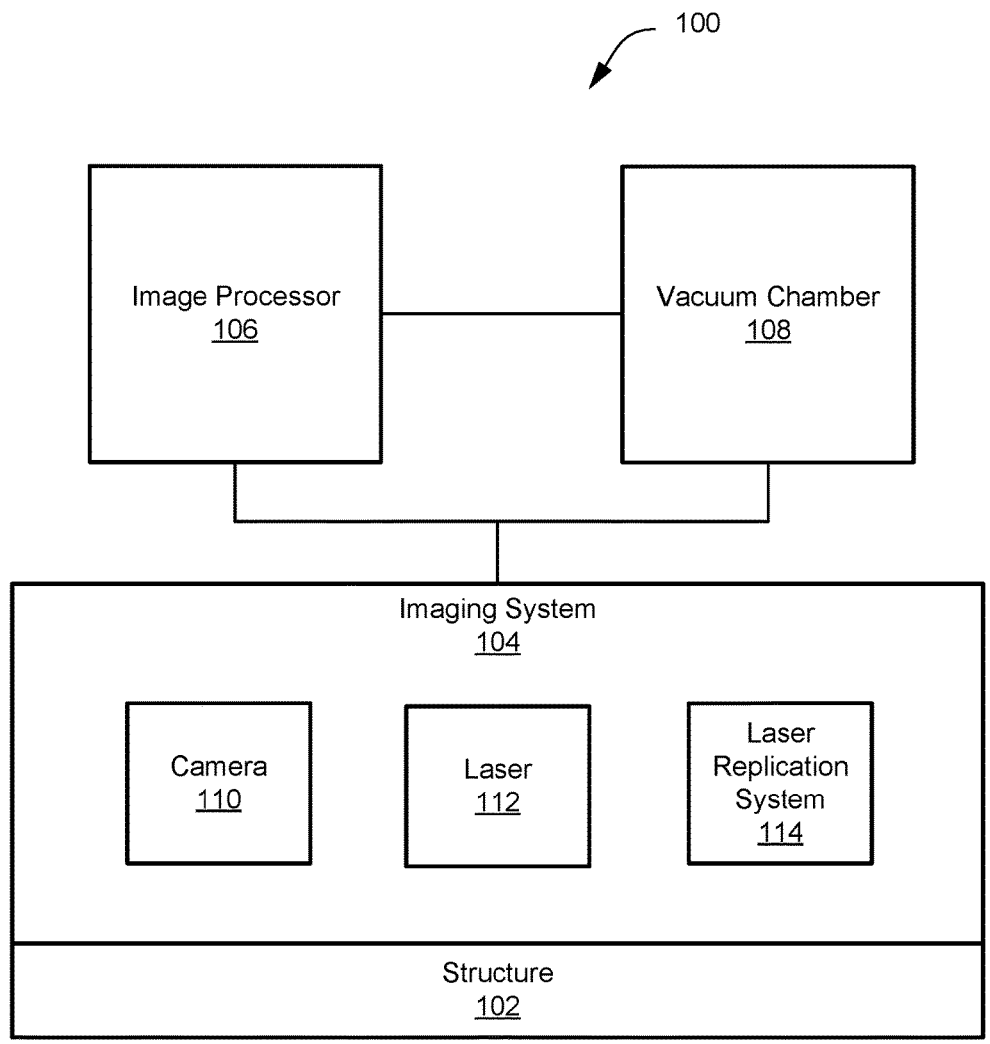
FIG. 1 is a schematic block diagram of a system for performing shearography non-destructive testing, according to one or more examples of the present disclosure.

As shown in FIG. 1, and according to one example, a system 100 for performing shearography non-destructive testing on a structure 102, is illustrated. The structure 102 may be any suitable structure, such as a portion of an aircraft (e.g., wing, fuselage, etc.), or another manufactured structure. The system 100 includes an imaging system 104 used to capture an image of the structure 102 and an image processor 106 that processes the image captured by the imaging system 104. The image processor 106 may be any suitable information handling device capable of processing the captured image. For example, the image processor 106 may be a computer, a smart phone, a processing device, or the like. The image processor 106 may include a processor for processing the captured image and a display for showing the captured image.

A vacuum chamber 108 may be coupled to the image processor 106 and the imaging system 104 to aid the imaging system 104 in capturing the image. For example, the vacuum chamber 108, in certain examples, may excite the structure 102 so that the imaging system 104 may capture an image of the structure 102 in an excited state. The image processor 106 may, in some implementations, compare the image of the structure 102 in the excited state to an image of the structure 102 in a non-excited state to detect defects in the structure 102. As used herein, the structure 102 (e.g., an object) may have a defect if there is a deformation on the surface of the structure 102, such as a deformation resulting from air trapped under the surface of the structure 102. The air trapped under the surface of the structure 102 may result from disbonded materials (e.g., lack of bonding between materials) under the surface of the structure 102.

The imaging system 104 includes a camera 110, a laser 112, and a laser replication system 114. The camera 110 is used to capture an image of the structure 102 and may be any suitable image capturing device. Moreover, the laser 112 is selectively operable to generate a laser beam used to illuminate the structure 102 prior to the camera 110 capturing the image of the structure 102. The laser 112 may be any suitable laser capable of being selectively operated to generate a laser beam, such as a gas laser, a chemical laser, a dye laser, a solid-state laser, a semiconductor laser, and so forth. The laser replication system 114 is used to receive a laser beam from the laser 112, divide the laser beam, and output portions of the laser beam that each have a substantially similar intensity, as explained in greater detail in FIGS. 3, 4, 5A, and 5B.

Figure 2:
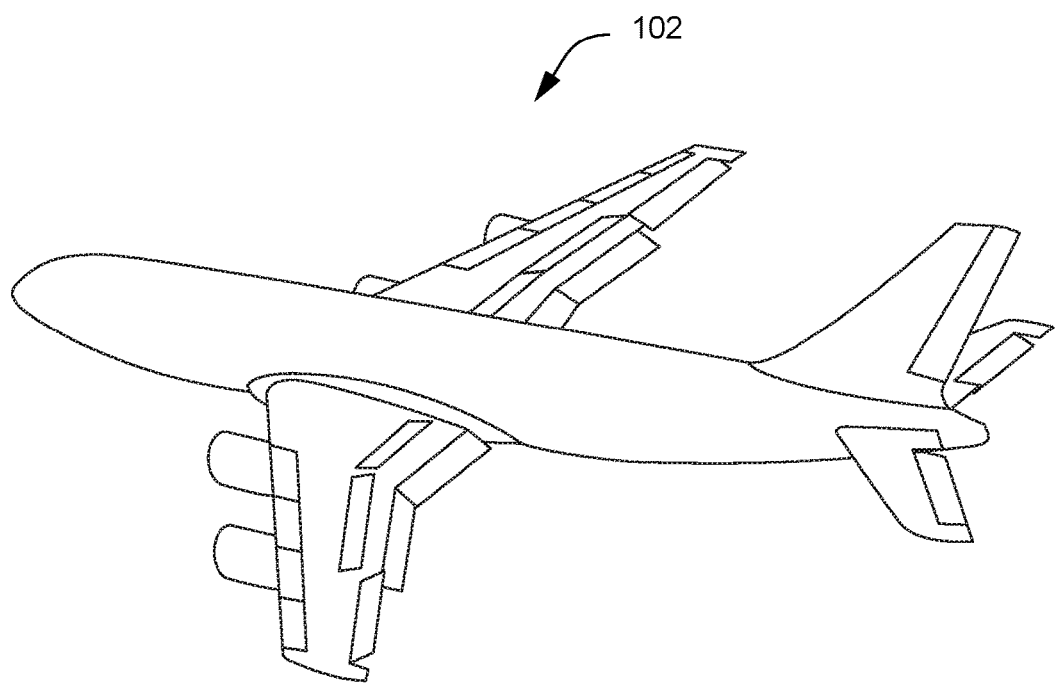
FIG. 2 is a perspective view of a structure on which shearography non-destructive testing may be performed, according to one or more examples of the present disclosure.

Referring to FIG. 2, and according to one example, the structure 102 on which non-destructive testing is performed may be an airplane, or the structure 102 may be any suitable manufactured device such as vehicles, aircraft, turbines, engines, and equipment operable in space like environments (e.g., satellite, rockets, missiles, space stations, space vehicles, space simulators). In certain examples, the structure 102 may be tested using non-destructive testing. In such examples, the structure 102 may be illuminated using the laser replication system 114. The laser replication system 114 may include a cavity, an input element coupled with the cavity and configured to receive a laser beam and to direct the laser beam into the cavity, and multiple output elements formed in the cavity and spaced apart along the cavity. Each output element of the multiple output elements may be configured to direct a portion of the laser beam out of the cavity such that each portion of the laser beam directed out of a respective one of the multiple output elements has a substantially similar intensity.

Figure 3:
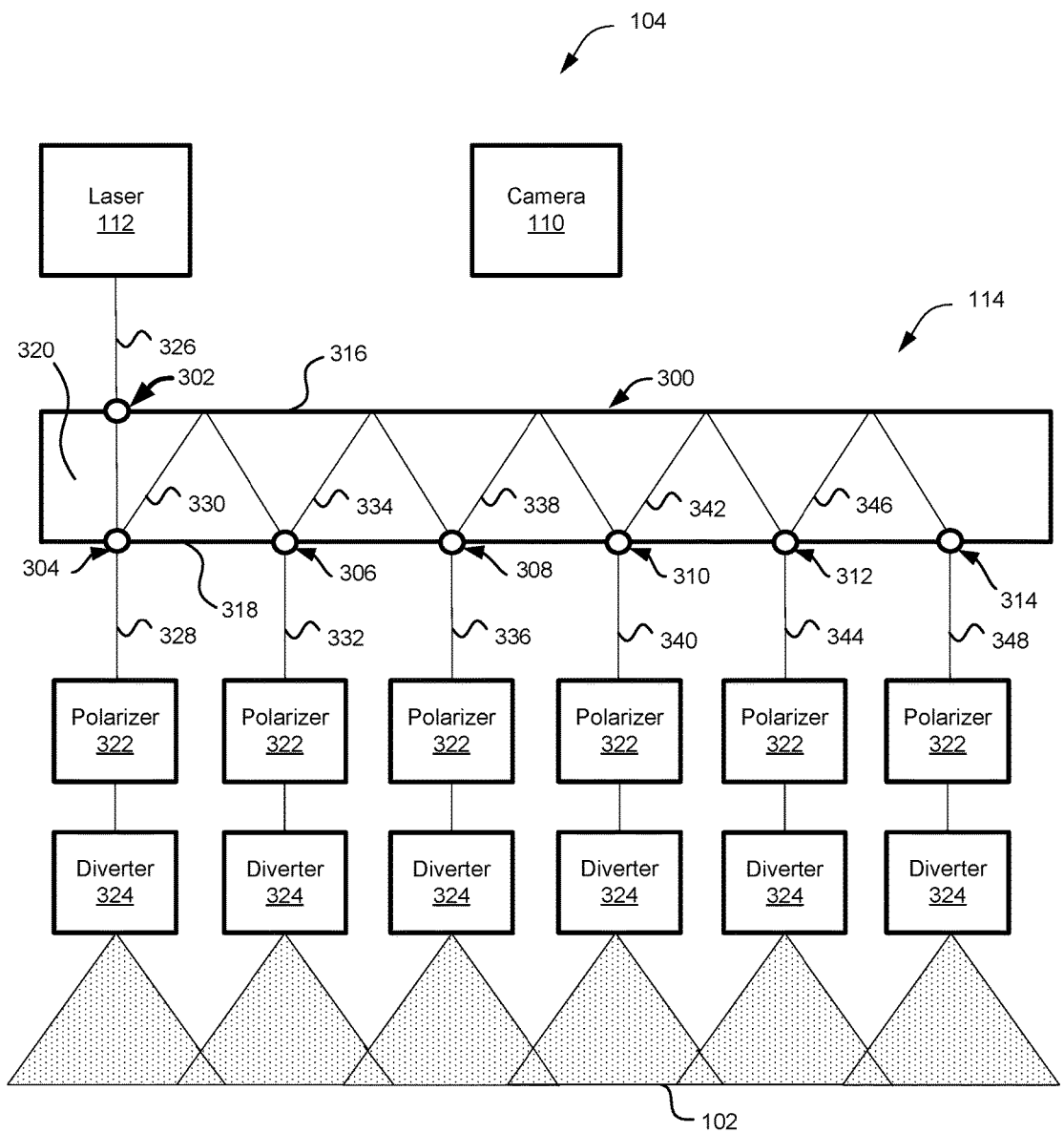
FIG. 3 is a schematic block diagram of an example of a laser replication system, according to one or more examples of the present disclosure.
Figure 5A:
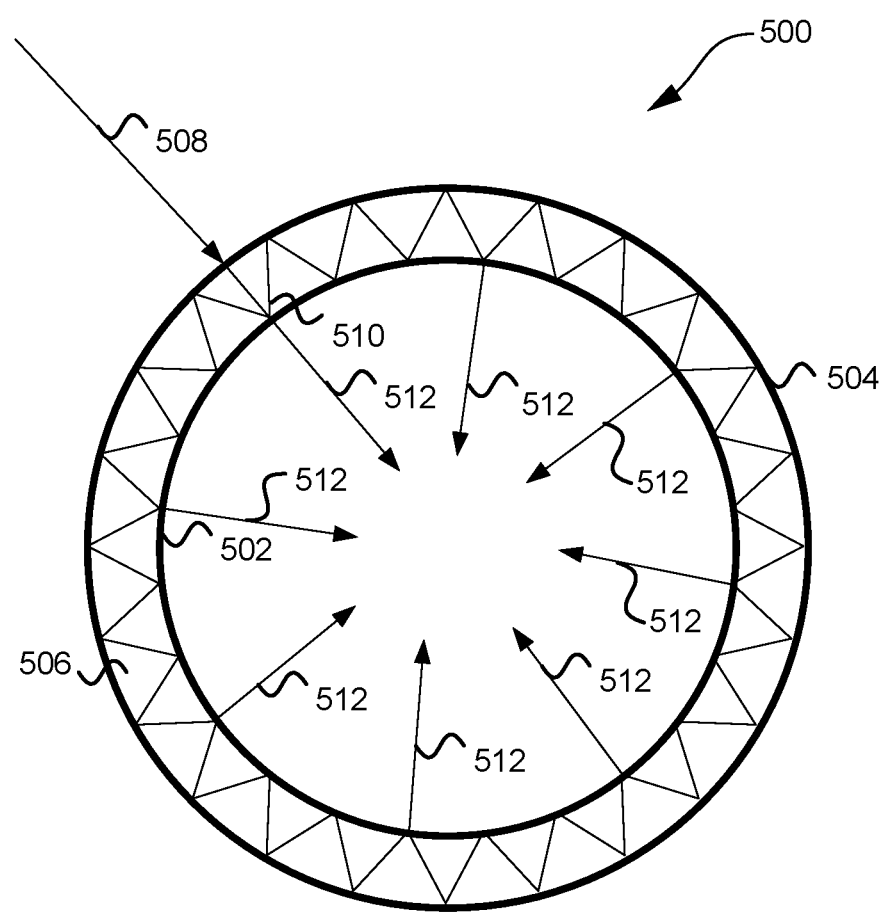
FIG. 5A is a schematic block diagram of an example of an annular shaped laser beam guide, according to one or more examples of the present disclosure.
Figure 5B:
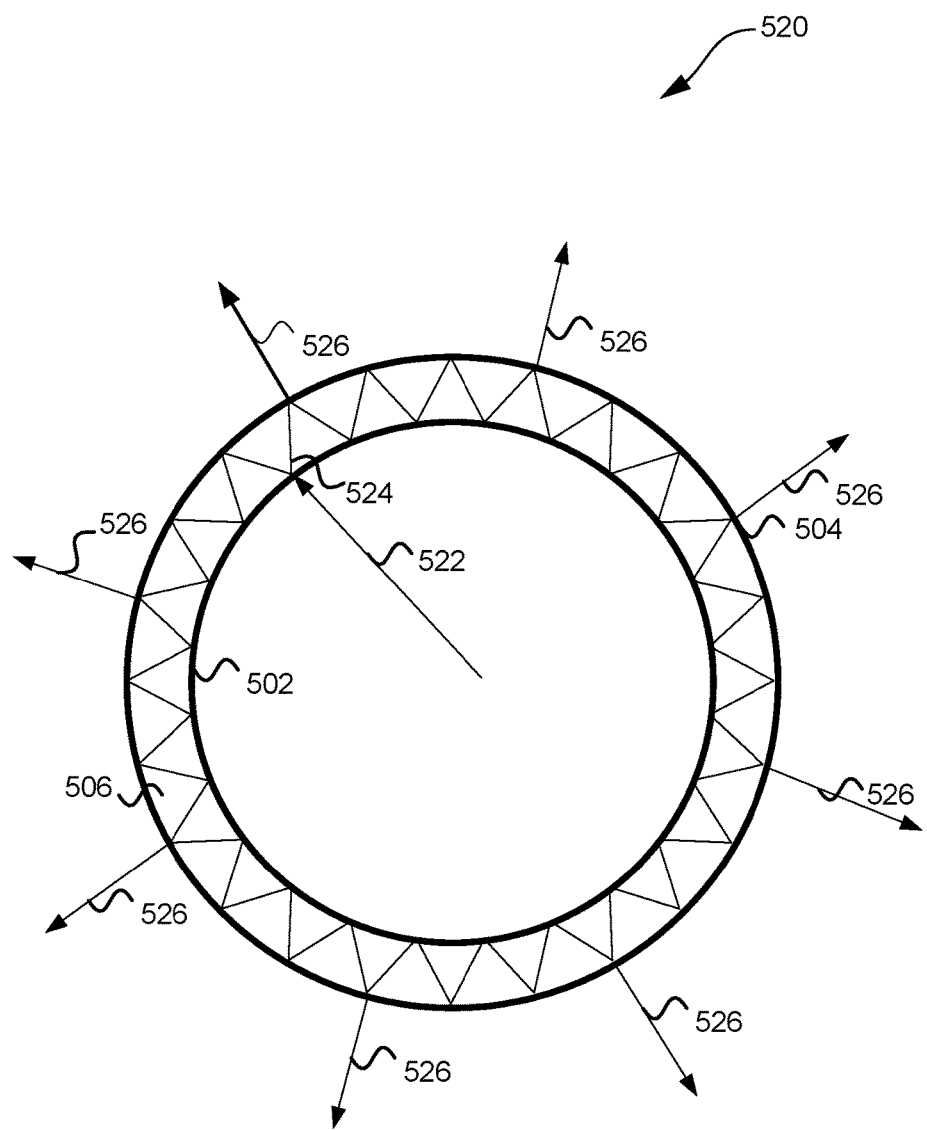
FIG. 5B is a schematic block diagram of another example of an annular shaped laser beam guide, according to one or more examples of the present disclosure.

Referring to FIG. 3, one example of a schematic block diagram of the laser replication system 114 is illustrated. The laser replication system 114 includes a planar shaped laser beam guide 300. It should be noted that while the laser beam guide 300 is substantially planar, in other implementations, the laser beam guide 300 may be shaped differently, such as being annular shaped as illustrated in FIGS. 5A and 5B. The laser beam guide 300 may be enclosed or partially enclosed.

The laser beam guide 300 includes an input element 302 and output elements 304, 306, 308, 310, 312, 314. Although six output elements 304, 306, 308, 310, 312, 314 are illustrated, any number of output elements greater than one may be part of the laser beam guide 300. The input element 302 and/or the output elements 304, 306, 308, 310, 312, 314 may include one or more of an aperture, a coating, and a material to facilitate a laser beam entering the laser beam guide 300 through the input element 302 and the laser beam exiting the laser beam guide 300 through one or more of the output elements 304, 306, 308, 310, 312, 314. For example, each of the output elements 304, 306, 308, 310, 312, 314 may include a material. The material of at least one of the output elements 304, 306, 308, 310, 312, 314 may be different from that of at least another of the output elements 304, 306, 308, 310, 312, 314. By having different materials among output elements 304, 306, 308, 310, 312, 314, the output elements 304, 306, 308, 310, 312, 314 may each output a different proportion of the laser beam that contacts the output elements 304, 306, 308, 310, 312, 314. The material may be any suitable material, such as a partially reflective material or a non-reflective material.

The input element 302 is positioned on a first side 316 of the laser beam guide 300 and the output elements 304, 306, 308, 310, 312, 314 are positioned on a second side 318 of the laser beam guide 300. In some implementations, the first side 316 of the laser beam guide 300 includes a reflective material or coating that reflects a laser beam. The first side 316 of the laser beam guide 300 and the second side 318 of the laser beam guide 300 enclose a cavity 320 through which the laser beam passes. As used herein, the first side 316 of the laser beam guide 300 may be considered a first side of the cavity 320, and the second side 318 of the laser beam guide 300 may be considered a second side of the cavity 320.

The input element 302 is coupled with the cavity 320, receives a laser beam, and directs the laser beam into the cavity 320. Moreover, the output elements 304, 306, 308, 310, 312, 314 are formed in the cavity 320 and spaced apart along the cavity 320. In some implementations, the output elements 304, 306, 308, 310, 312, 314 are spaced apart from an adjacent output element by a substantially equal distance. The substantially equal distance may be a distance that varies by less than 1, 2, 5, 10, or 15 percent.

Portions of the laser beam that exit the laser beam guide 300 may be directed through a polarizer 322 and/or through a diverter 324 (e.g., laser beam diverter), as illustrated. The polarizer 322 is positioned between the output elements 304, 306, 308, 310, 312, 314 and the diverter 324. There may be any suitable number of polarizers 322, such as one polarizer 322 for the entire laser beam guide 300 or one polarizer 322 for each of the output elements 304, 306, 308, 310, 312, 314. In certain implementations, the polarizer 322 is used to polarize a portion of the laser beam that exits each of the output elements 304, 306, 308, 310, 312, 314. In some implementations, the polarizer 322 polarizes the portion of the laser beam that exits each of the output elements 304, 306, 308, 310, 312, 314 in a substantially similar direction. For example, the polarizer 322 may polarize the portion of the laser beam that exits each of the output elements 304, 306, 308, 310, 312, 314 in a direction that is within 1, 2, 5, or 10 degrees from other output elements. In various implementations, the polarizer 322 polarizes the portion of the laser beam that exits each of the output elements 304, 306, 308, 310, 312, 314 to be polarized in multiple different direction (e.g., scattered).

The diverter 324 may diffuse a portion of the laser beam that exits each of the output elements 304, 306, 308, 310, 312, 314. There may be any suitable number of diverters 324, such as one diverter 324 for the entire laser beam guide 300 or one diverter 324 for each of the output elements 304, 306, 308, 310, 312, 314.

During operation, the laser 112 directs a laser beam 326 through the input element 302 into the cavity 320. The laser beam 326 travels through the cavity 320 and contacts the output element 304. The output element 304 directs a first portion 328 of the laser beam 326 out of the cavity 320 and reflects a second portion 330 of the laser beam 326 into the cavity 320. The output element 304 may include a partially reflective material that directs the first portion 328 of the laser beam 326 out of the cavity 320 and reflects the second portion 330 of the laser beam 326 into the cavity 320. In some implementations, the first portion 328 of the laser beam 326 may be approximately 17 percent (e.g., ⅙) of the laser beam 326, and the second portion 330 of the laser beam 326 may be approximately 83 percent (e.g., ⅚) of the laser beam 326. Although various percentages are used herein to describe a proportion of a laser beam, these percentages are for example purposes only, and in various examples may be any suitable percentage. Moreover, the second portion 330 of the laser beam 326 may be considered the remaining portion of the laser beam 326 that remains in the cavity 320.

The second portion 330 of the laser beam 326 reflects off of the first side 316 of the laser beam guide 300 and contacts the output element 306. The output element 306 directs a third portion 332 of the laser beam 326 out of the cavity 320 and reflects a fourth portion 334 of the laser beam 326 into the cavity 320. The output element 306 may include a partially reflective material that directs the third portion 332 of the laser beam 326 out of the cavity 320 and reflects the fourth portion 334 of the laser beam 326 into the cavity 320. In some implementations, the third portion 332 of the laser beam 326 may be approximately 20 percent (e.g., 1/5) of the second portion 330 of the laser beam 326, and the fourth portion 334 of the laser beam 326 may be approximately 80 percent (e.g., 4/5) of the second portion 330 of the laser beam 326. Accordingly, the third portion 332 of the laser beam 326 may be approximately the same percentage of the original laser beam 326 as the first portion 328 of the laser beam 326. Therefore, the first portion 328 of the laser beam 326 and the third portion 332 of the laser beam 326 may have substantially similar intensity, energy, and/or power. As used herein, having a substantially similar intensity, energy, and/or power may mean that the intensity, energy, and/or power may be within 1, 2, 5, or 10 percent of one another. Moreover, the fourth portion 334 of the laser beam 326 may be considered the remaining portion of the laser beam 326 that remains in the cavity 320.

The fourth portion 334 of the laser beam 326 reflects off of the first side 316 of the laser beam guide 300 and contacts the output element 308. The output element 308 directs a fifth portion 336 of the laser beam 326 out of the cavity 320 and reflects a sixth portion 338 of the laser beam 326 into the cavity 320. The output element 308 may include a partially reflective material that directs the fifth portion 336 of the laser beam 326 out of the cavity 320 and reflects the sixth portion 338 of the laser beam 326 into the cavity 320. In some implementations, the fifth portion 336 of the laser beam 326 may be approximately 25 percent (e.g., 1/4) of the fourth portion 334 of the laser beam 326, and the sixth portion 338 of the laser beam 326 may be approximately 75 percent (e.g., 3/4) of the fourth portion 334 of the laser beam 326. Accordingly, the fifth portion 336 of the laser beam 326 may be approximately the same percentage of the original laser beam 326 as the first and third portions 328, 332 of the laser beam 326. Therefore, the first portion 328 of the laser beam 326, the third portion 332 of the laser beam 326, and the fifth portion 336 of the laser beam 326 may have substantially similar intensity, energy, and/or power. Moreover, the sixth portion 338 of the laser beam 326 may be considered the remaining portion of the laser beam 326 that remains in the cavity 320.

The sixth portion 338 of the laser beam 326 reflects off of the first side 316 of the laser beam guide 300 and contacts the output element 310. The output element 310 directs a seventh portion 340 of the laser beam 326 out of the cavity 320 and reflects an eighth portion 342 of the laser beam 326 into the cavity 320. The output element 310 may include a partially reflective material that directs the seventh portion 340 of the laser beam 326 out of the cavity 320 and reflects the eighth portion 342 of the laser beam 326 into the cavity 320. In some implementations, the seventh portion 340 of the laser beam 326 may be approximately 33 percent (e.g., 1/3) of the sixth portion 338 of the laser beam 326, and the eighth portion 342 of the laser beam 326 may be approximately 67 percent (e.g., 2/3) of the sixth portion 338 of the laser beam 326. Accordingly, the seventh portion 340 of the laser beam 326 may be approximately the same percentage of the original laser beam 326 as the first, third, and fifth portions 328, 332, 336 of the laser beam 326. Therefore, the first portion 328 of the laser beam 326, the third portion 332 of the laser beam 326, the fifth portion 336 of the laser beam 326, and the seventh portion 340 of the laser beam 326 may have substantially similar intensity, energy, and/or power. Moreover, the eighth portion 342 of the laser beam 326 may be considered the remaining portion of the laser beam 326 that remains in the cavity 320.

The eighth portion 342 of the laser beam 326 reflects off of the first side 316 of the laser beam guide 300 and contacts the output element 312. The output element 312 directs a ninth portion 344 of the laser beam 326 out of the cavity 320 and reflects a tenth portion 346 of the laser beam 326 into the cavity 320. The output element 312 may include a partially reflective material that directs the ninth portion 344 of the laser beam 326 out of the cavity 320 and reflects the tenth portion 346 of the laser beam 326 into the cavity 320. In some implementations, the ninth portion 344 of the laser beam 326 may be approximately 50 percent (e.g., 1/2) of the eighth portion 342 of the laser beam 326, and the tenth portion 346 of the laser beam 326 may be approximately 50 percent (e.g., 1/2) of the eighth portion 342 of the laser beam 326. Accordingly, the ninth portion 344 of the laser beam 326 may be approximately the same percentage of the original laser beam 326 as the first, third, fifth, and seventh portions 328, 332, 336, 340 of the laser beam 326. Therefore, the first portion 328 of the laser beam 326, the third portion 332 of the laser beam 326, the fifth portion 336 of the laser beam 326, the seventh portion 340 of the laser beam 326, and the ninth portion 344 of the laser beam 326 may have substantially similar intensity, energy, and/or power. Moreover, the tenth portion 346 of the laser beam 326 may be considered the remaining portion of the laser beam 326 that remains in the cavity 320.

The tenth portion 346 of the laser beam 326 reflects off of the first side 316 of the laser beam guide 300 and contacts the output element 314. The output element 314 directs an eleventh portion 348 of the laser beam 326 out of the cavity 320. The output element 314 may include a non-reflective material that directs the eleventh portion 348 of the laser beam 326 out of the cavity 320. In some implementations, the eleventh portion 348 of the laser beam 326 may be approximately 100 percent of the tenth portion 346 of the laser beam 326. Accordingly, the eleventh portion 348 of the laser beam 326 may be approximately the same percentage of the original laser beam 326 as the first, third, fifth, seventh, and ninth portions 328, 332, 336, 340, 344 of the laser beam 326. Therefore, the first portion 328 of the laser beam 326, the third portion 332 of the laser beam 326, the fifth portion 336 of the laser beam 326, the seventh portion 340 of the laser beam 326, the ninth portion 344 of the laser beam 326, and the eleventh portion 348 of the laser beam 326 may have substantially similar intensity, energy, and/or power. In various implementations, the first portion 328 of the laser beam 326, the third portion 332 of the laser beam 326, the fifth portion 336 of the laser beam 326, the seventh portion 340 of the laser beam 326, the ninth portion 344 of the laser beam 326, and the eleventh portion 348 of the laser beam 326 may have a substantially similar phase (e.g., may be in phase with one another). As used herein, a substantially similar phase may mean that phases are within 1, 2, 5, or 10 degrees of one another.

Accordingly, each of the output elements 304, 306, 308, 310, 312, 314 directs a portion of the laser beam 326 out of the cavity 320 such that each portion of the laser beam directed out of a respective one of the output elements 304, 306, 308, 310, 312, 314 has a substantially similar intensity, energy, and/or power.

It should be noted that the partially reflective materials of the output elements 304, 306, 308, 310, 312 may have different reflective properties to result in directing (e.g., allowing to pass) different percentages of the laser beam 326 through the output elements 304, 306, 308, 310, 312. For example, the output element 304 may include a partially reflective material that is more opaque than the partially reflective material of the output element 306. As another example, the output element 306 may include a partially reflective material that is more opaque than the partially reflective material of the output element 308. As a further example, the output element 308 may include a partially reflective material that is more opaque than the partially reflective material of the output element 310. As an additional example, the output element 310 may include a partially reflective material that is more opaque than the partially reflective material of the output element 312. As used herein, opaque may refer to not being transparent, or blocking a portion of a laser beam from passing through a material. For example, if a first material is more opaque than a second material, the first material blocks a greater percentage of a laser beam from passing therethrough. Moreover, as used herein, opacity may refer to how opaque a material is. For example, a material that has a higher opacity is more opaque than a material with a lower opacity. The opacity of a material of the output elements 304, 306, 308, 310, 312, 314 through which the laser beam passes may vary such that the output elements 304, 306, 308, 310, 312, 314 are ordered in descending opacity from highest opacity (e.g., output element 304) to lowest opacity (e.g., output element 314). The lowest opacity may block a low percentage, or no percentage, of a laser beam from passing therethrough.

After the portions of the laser beam 326 exit the output elements 304, 306, 308, 310, 312, 314, each portion of the laser beam 326 may pass through a polarizer 322 and/or a diverter 324 before illuminating the structure 102. While the structure 102 is illuminated, the camera 110, positioned to capture an image of the structure 102, may capture an image illuminated by the portions of the laser beam 326.

Figure 4:
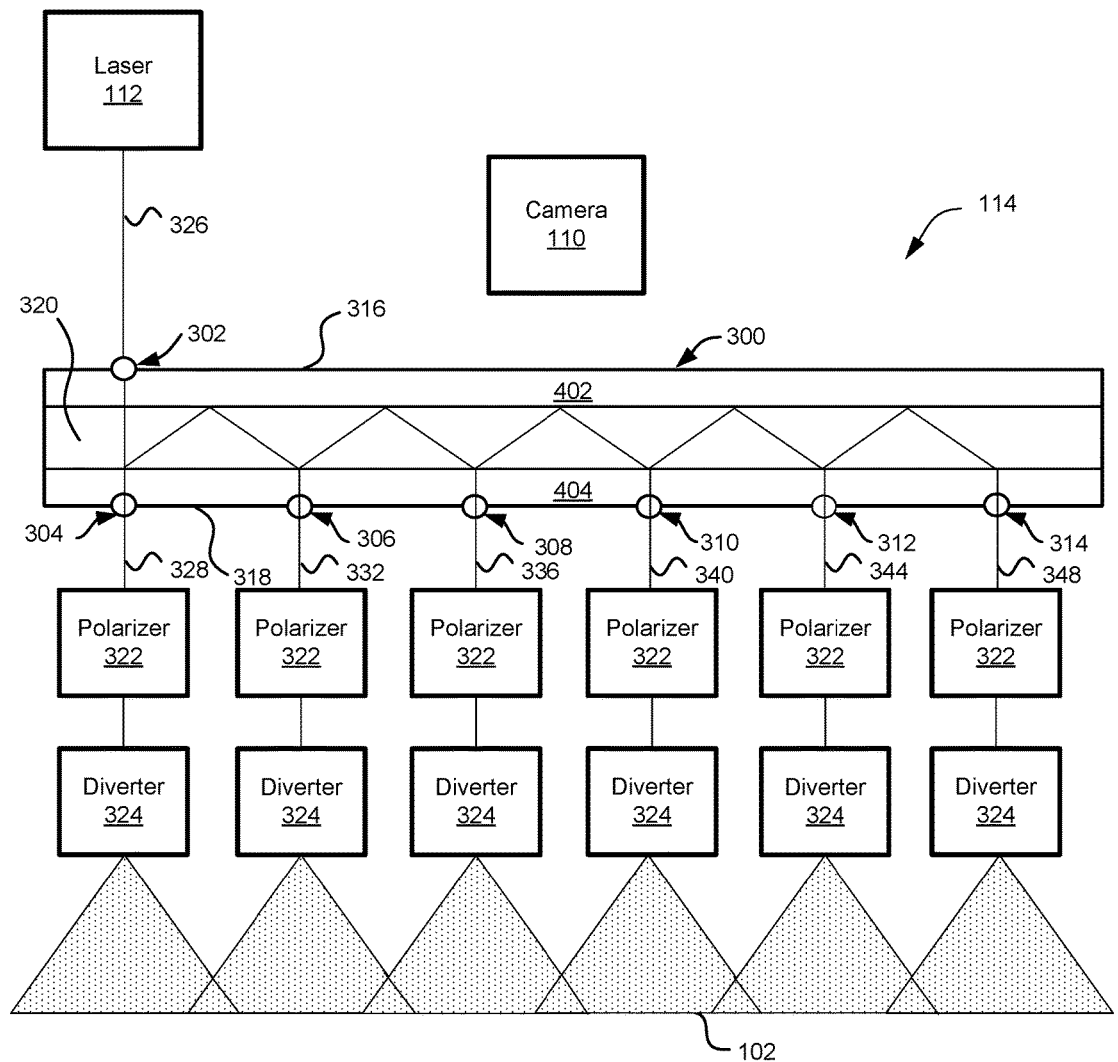
FIG. 4 is a schematic block diagram of another example of a laser replication system, according to one or more examples of the present disclosure.

Turning to FIG. 4, another example of a schematic block diagram of the laser replication system 114 is illustrated. The laser replication system 114 includes the laser beam guide 300, the polarizer 322, the diverter 324, the camera 110, and the laser 112, which may be substantially similar to the laser beam guide 300, the polarizer 322, the diverter 324, the camera 110, and the laser 112 previously described.

Moreover, the laser beam guide 300 of FIG. 4 includes a first material 402 disposed on the first side 316 of the laser beam guide 300 and a second material 404 disposed on the second side 318 of the laser beam guide 300. The first material 402 may be a substantially reflective material that is designed to reflect a laser beam 326. The second material 404 may be a partially reflective material that varies along the length of the laser beam guide 300. For example, the second material 404 may reflect a large percentage of the laser beam 326 that contacts a point adjacent to the output element 304 and the second material 404 may reflect a small percentage (e.g., zero) of the laser beam 326 that contacts a point adjacent to the output element 314. In some examples, the second material 404 may include a varying amount of a substance that results in a highest opacity adjacent to the output element 304, a second highest opacity adjacent to the output element 306, a third highest opacity adjacent to the output element 308, a fourth highest opacity adjacent to the output element 310, a fifth highest opacity adjacent to the output element 312, and a sixth highest opacity (e.g., lowest opacity) adjacent to the output element 314.

Referring to FIG. 5A, one example of a schematic block diagram of an annular shaped laser beam guide 500 is illustrated. The laser beam guide 500 includes a first side 502, a second side 504, and a cavity 506 between the first and second sides 502, 504. The laser beam guide 500 receives a laser beam 508 through an input element positioned on the second side 504 that directs the laser beam into the cavity 506 of the laser beam guide 500, illustrated by reflecting laser beam 510. Portions 512 of the laser beam 508 are directed out of the laser beam guide 500 through output elements positioned on the first side 502. Each portion 512 of the laser beam 508 directed out of the laser beam guide 500 may have a substantially similar intensity, energy, and/or power. As illustrated, the portions 512 of the laser beam 508 are directed out of the laser beam guide 500 toward a central region of the laser beam guide 500 to illuminate a structure that may be placed therein.

Referring to FIG. 5B, another example of a schematic block diagram of an annular shaped laser beam guide 520 is illustrated. The laser beam guide 520 includes a first side 502, a second side 504, and a cavity 506 between the first and second sides 502, 504. The laser beam guide 520 receives a laser beam 522 through an input element positioned on the first side 502 that directs the laser beam into the cavity 506 of the laser beam guide 520, illustrated by reflecting laser beam 524. Portions 526 of the laser beam 522 are directed out of the laser beam guide 520 through output elements. Each portion 526 of the laser beam 522 directed out of the laser beam guide 520 may have a substantially similar intensity, energy, and/or power. As illustrated, the portions 526 of the laser beam 522 are directed out of the laser beam guide 520 in a radiating fashion to illuminate a structure that may be placed around the laser beam guide 520.

Figure 6:
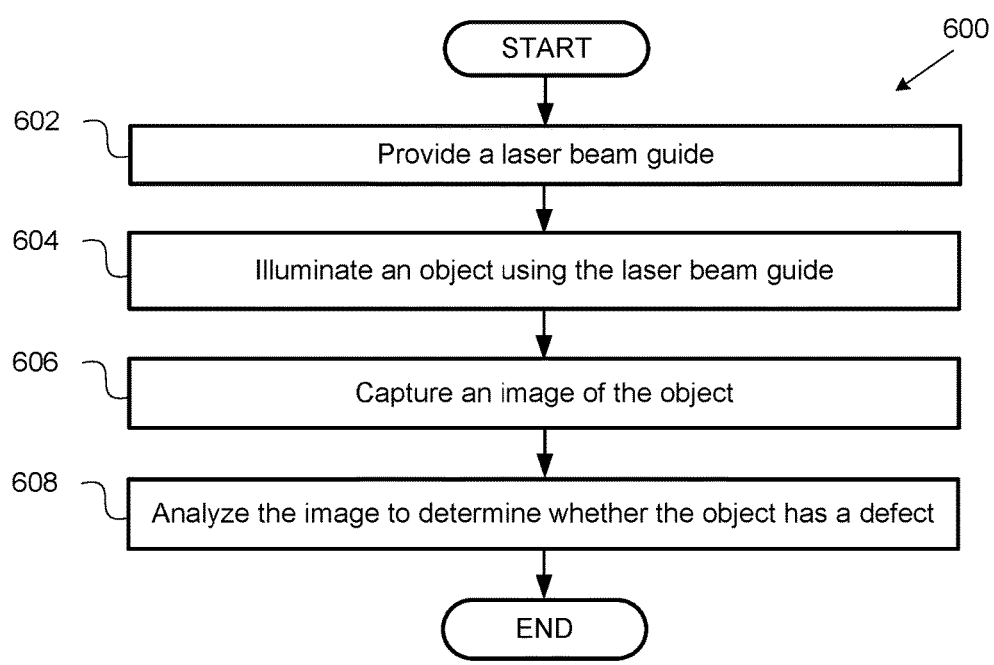
FIG. 6 is a schematic flow diagram of a method of non-destructive testing of an object, according to one or more examples of the present disclosure.

Referring to FIG. 6, one example of a method 600 of non-destructive testing of an object is shown. The method 600 includes providing a laser beam guide at 602. The laser beam guide may include a cavity, an input element coupled with the cavity and configured to receive a laser beam and to direct the laser beam into the cavity, and multiple output elements formed in the cavity and spaced apart along the cavity. Each output element of the multiple output elements is configured to direct a portion of the laser beam out of the cavity such that each portion of the laser beam directed out of a respective one of the multiple output elements has a substantially similar intensity.

Additionally, the method 600 includes illuminating an object using the laser beam guide at 604. Then, the method 600 may include capturing an image of the object at 606. The object may be illuminated by each portion of the laser beam directed out of the respective ones of the multiple output elements. The method 600 also includes analyzing the image to determine whether the object has a defect at 608.

In certain implementations, analyzing the image to determine whether the object has a defect includes measuring out-of-plane displacement. As used herein, out-of-plane displacement may refer to a portion of a structure that is out of place in a direction perpendicular to a surface of the structure.

In some implementations, measuring the out-of-plane displacement includes using image subtraction to subtract a change in a surface of the object detected via optical fringes. For example, two images may be obtained and a first image may be subtracted from a second image. The first image may be a first speckle image showing optical fringes that is obtained in a nominal (e.g., non-excited) state and the second image may be a second speckle image showing optical fringes that is obtained in an excited state. The first speckle image may be subtracted from the second speckle image using speckle subtraction. Out-of-plane displacement may be detected in the object by analyzing the optical fringes in the image produced from subtracting the first image from the second image. As used herein, optical fringes may refer to light and/or dark bands produced by the interference and diffraction of light.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

The schematic flow chart diagrams included herein are generally set forth as logical flow chart diagrams. As such, the depicted order and labeled steps are indicative of one example of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of computer readable program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing.

In one example, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present subject matter may be embodied in other specific forms without departing from its spirit or essential characteristics. The described examples are to be considered in all respects only as illustrative and not restrictive. All changes which come within the meaning and range of equivalency of the claims are to be embraced within their scope.

What is claimed is:

1. An apparatus, comprising:
a cavity having an annular shape, wherein the cavity is disposed within a first annular shaped side of a beam guide and a second annular shaped side of the beam guide;
an input element comprising an input aperture coupled with the cavity and configured to receive a laser beam and to direct the laser beam into the cavity; and
a plurality of output elements, wherein each output element of the plurality of output elements comprises an output aperture formed in the cavity and the plurality of output elements are spaced apart along the cavity, each output element of the plurality of output elements is configured to direct a portion of the laser beam out of the cavity such that each portion of the laser beam directed out of a respective one of the plurality of output elements has a substantially similar intensity, the substantially similar intensity comprises being within ten percent of other intensities of the plurality of output elements, at least one output element of the plurality of output elements comprises a partially reflective material, and a first portion of the laser beam is directed through the partially reflective material and a second portion of the laser beam is reflected by the partially reflective material.

2. The apparatus of claim 1, wherein:
each of the plurality of output elements comprises a material; and
the material of at least one of the output elements of the plurality of output elements is different from that of at least another of the output elements of the plurality of output elements.

3. The apparatus of claim 1, wherein:
a first output element of the plurality of output elements comprises the partially reflective material;
a last output element of the plurality of output elements comprises a non-reflective material through which a remaining portion of the laser beam is directed out of the cavity; and
the first portion of the laser beam and the remaining portion of the laser beam comprise substantially similar intensities.

4. The apparatus of claim 1, wherein:
a first output element of the plurality of output elements comprises a first partially reflective material that directs the first portion of the laser beam out of the cavity;
a second output element of the plurality of output elements comprises a second partially reflective material that directs a second portion of the laser beam out of the cavity; and
the first and second partially reflective materials comprise different reflective properties, and the first portion of the laser beam and the second portion of the laser beam comprise substantially similar intensities.

5. The apparatus of claim 4, wherein:
the first portion of the laser beam is directed out of the cavity before the second portion of the laser beam is directed out of the cavity;
the first portion of the laser beam comprises a first percentage of the laser beam;
a remaining portion of the laser beam remains in the cavity after the first portion of the laser beam is directed out of the cavity;
the second portion of the laser beam comprises a second percentage of the remaining portion of the laser beam; and
the second percentage is greater than the first percentage.

6. The apparatus of claim 1, wherein the cavity is enclosed.

7. The apparatus of claim 1, wherein each output element of the plurality of output elements is spaced apart from an adjacent output element of the plurality of output elements by a substantially equal distance.

8. The apparatus of claim 1, wherein:
the cavity comprises a first side and a second side, opposite the first side;
the input element is disposed on the first side of the cavity; and
the plurality of output elements are disposed on the second side of the cavity.

9. The apparatus of claim 8, wherein an interior surface of the first side of the cavity comprises a reflective coating.

10. The apparatus of claim 8, wherein an interior surface of the second side of the cavity comprises a partially reflective material having an opacity that varies from a first opacity to a second opacity, the first opacity being greater than the second opacity.

11. A system, comprising:
a laser, selectively operable to generate a laser beam;
an apparatus, comprising:
   a cavity having an annular shape, wherein the cavity is disposed within a first annular shaped side of a beam guide and a second annular shaped side of the beam guide;
   an input element comprising an input aperture coupled with the cavity and configured to receive the laser beam and to direct the laser beam into the cavity; and
   a plurality of output elements, wherein each output element of the plurality of output elements comprises an output aperture formed in the cavity and the plurality of output elements are spaced apart along the cavity, each output element of the plurality of output elements is configured to direct a portion of the laser beam out of the cavity such that each portion of the laser beam directed out of a respective one of the plurality of output elements has a substantially similar intensity, the substantially similar intensity comprises being within ten percent of other intensities of the plurality of output elements, at least one output element of the plurality of output elements comprises a partially reflective material, and a first portion of the laser beam is directed through the partially reflective material and a second portion of the laser beam is reflected by the partially reflective material; and
at least one laser beam diverter configured to diffuse the portion of the laser beam that exits each output element of the plurality of output elements.

12. The system of claim 11, wherein the at least one laser beam diverter comprises a plurality of laser beam diverters each configured to diffuse the portion of the laser beam that exits a respective one of the plurality of output elements.

13. The system of claim 11, further comprising at least one polarizer positioned between the plurality of output elements and the at least one laser beam diverter, wherein the at least one polarizer is configured to polarize the portion of the laser beam that exits each output element of the plurality of output elements.

14. The system of claim 13, wherein the at least one polarizer is configured to polarize the portion of the laser beam that exits each output element of the plurality of output elements to be polarized in a substantially similar direction.

15. The system of claim 13, wherein the at least one polarizer is configured to polarize the portion of the laser beam that exits each output element of the plurality of output elements to be polarized in a plurality of directions.

16. The system of claim 11, further comprising a camera configured to capture an image illuminated by each portion of the laser beam exiting each output element of the plurality of output elements.

17. The system of claim 11, wherein each portion of the laser beam exiting each output element of the plurality of output elements has a substantially similar phase.

18. A method of non-destructive testing of an object, comprising:
illuminating an object using an apparatus, wherein the apparatus comprises:
   a cavity having an annular shape, the cavity is disposed within a first annular shaped side of a beam guide and a second annular shaped side of the beam guide;
   an input element comprising an input aperture coupled with the cavity and configured to receive a laser beam and to direct the laser beam into the cavity; and
   a plurality of output elements, wherein each output element of the plurality of output elements comprises an output aperture formed in the cavity and the plurality of output elements are spaced apart along the cavity, each output element of the plurality of output elements is configured to direct a portion of the laser beam out of the cavity such that each portion of the laser beam directed out of a respective one of the plurality of output elements has a substantially similar intensity, the substantially similar intensity comprises being within ten percent of other intensities of the plurality of output elements, at least one output element of the plurality of output elements comprises a partially reflective material, and a first portion of the laser beam is directed through the partially reflective material and a second portion of the laser beam is reflected by the partially reflective material;
capturing an image of the object illuminated by each portion of the laser beam directed out of the respective one of the plurality of output elements; and
analyzing the image to determine whether the object has a defect.

19. The method of claim 18, wherein analyzing the image to determine whether the object has a defect comprises measuring out-of-plane displacement.

20. The method of claim 19, wherein measuring the out-of-plane displacement comprises using image subtraction to subtract a change in a surface of the object detected via optical fringes.

* * * * *